US010251915B2

(12) United States Patent
Opara et al.

(10) Patent No.: US 10,251,915 B2
(45) Date of Patent: *Apr. 9, 2019

(54) CO-ENCAPSULATION OF LIVE CELLS WITH OXYGEN-GENERATING PARTICLES

(71) Applicant: Wake Forest University Health Sciences, Winston-Salem, NC (US)

(72) Inventors: Emmanuel C. Opara, Durham, NC (US); Benjamin S. Harrison, Tobaccoville, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/689,268

(22) Filed: Aug. 29, 2017

(65) Prior Publication Data

US 2017/0354691 A1  Dec. 14, 2017

Related U.S. Application Data

(63) Continuation of application No. 15/411,351, filed on Jan. 20, 2017, now Pat. No. 9,775,866, which is a (Continued)

(51) Int. Cl.
*A61K 35/39* (2015.01)
*C12N 5/071* (2010.01)
(Continued)

(52) U.S. Cl.
CPC ............ *A61K 35/39* (2013.01); *A61K 9/0024* (2013.01); *A61K 9/501* (2013.01); *A61K 9/5015* (2013.01);
(Continued)

(58) Field of Classification Search
CPC ........ A61K 35/39; A61K 45/06; A61K 9/501; A61K 9/0024; A61K 9/5015; A61K 47/22;
(Continued)

(56) References Cited

U.S. PATENT DOCUMENTS 4,352,883 A   10/1982  Lim
4,673,566 A    6/1987  Goosen et al.
(Continued)

FOREIGN PATENT DOCUMENTS

WO   WO 2010/078569 A2   7/2010
WO   WO 2010/121024 A2  10/2010

OTHER PUBLICATIONS

International Search Report an Written Opinion, PCT/US2012/050060, dated Oct. 23, 2012.

*Primary Examiner* — Trevor Love
(74) *Attorney, Agent, or Firm* — Myers Bigel, P.A.

(57) ABSTRACT

Microcapsules are described that comprise (a) a liquid aqueous or hydrogel core; (b) a semipermeable membrane surrounding said core; (c) live animal cells (e.g., pancreatic cells) in the core; and (d) oxygen-generating particles in said core, said oxygen-generating particles included in said microcapsules in an amount sufficient to lengthen the duration of viability of said animal cells in said microcapsules. Compositions comprising such microcapsules and uses thereof, such as in treating diabetes, are also described.

12 Claims, 4 Drawing Sheets

Comparison of CaO₂ and MgO₂ release over six days, dissolved oxygen readings are an average of 5 sample groups with 1500 microcapsules each.

Related U.S. Application Data continuation of application No. 15/183,037, filed on Jun. 15, 2016, now Pat. No. 9,561,254, which is a continuation of application No. 14/237,214, filed as application No. PCT/US2012/050060 on Aug. 9, 2012, now Pat. No. 9,393,272.

(60) Provisional application No. 61/601,780, filed on Feb. 22, 2012, provisional application No. 61/521,420, filed on Aug. 9, 2011.

(51) Int. Cl.

| | |
|---|---|
| *A61K 45/06* | (2006.01) |
| *A61K 9/50* | (2006.01) |
| *A61K 9/00* | (2006.01) |
| *A61K 47/22* | (2006.01) |
| *A61K 38/18* | (2006.01) |
| *A61K 47/02* | (2006.01) |
| *A61K 47/42* | (2017.01) |
| *A61K 38/44* | (2006.01) |
| *A61K 31/555* | (2006.01) |
| *A61K 33/40* | (2006.01) |
| *C12N 1/04* | (2006.01) |
| *C12N 11/10* | (2006.01) |
| *C12N 11/04* | (2006.01) |

(52) U.S. Cl.
CPC .......... *A61K 9/5036* (2013.01); *A61K 9/5073* (2013.01); *A61K 31/555* (2013.01); *A61K 33/40* (2013.01); *A61K 38/1866* (2013.01); *A61K 38/44* (2013.01); *A61K 45/06* (2013.01); *A61K 47/02* (2013.01); *A61K 47/22* (2013.01); *A61K 47/42* (2013.01); *C12N 1/04* (2013.01); *C12N 5/0676* (2013.01); *C12N 11/04* (2013.01); *C12N 11/10* (2013.01)

(58) Field of Classification Search
CPC .. A61K 9/5073; A61K 38/1866; A61K 47/02; A61K 47/42; A61K 38/44; A61K 9/5036; A61K 31/555; A61K 33/40; C12N 5/0676; C12N 1/04; C12N 11/10; C12N 11/04

See application file for complete search history.

(56) References Cited

U.S. PATENT DOCUMENTS

| | | |
|---|---|---|
| 6,140,089 A | 10/2000 | Aebischer et al. |
| 6,783,964 B2 | 8/2004 | Opara |
| 2010/0112087 A1 | 5/2010 | Harrison et al. |
| 2012/0213708 A1 | 8/2012 | Anderson et al. |

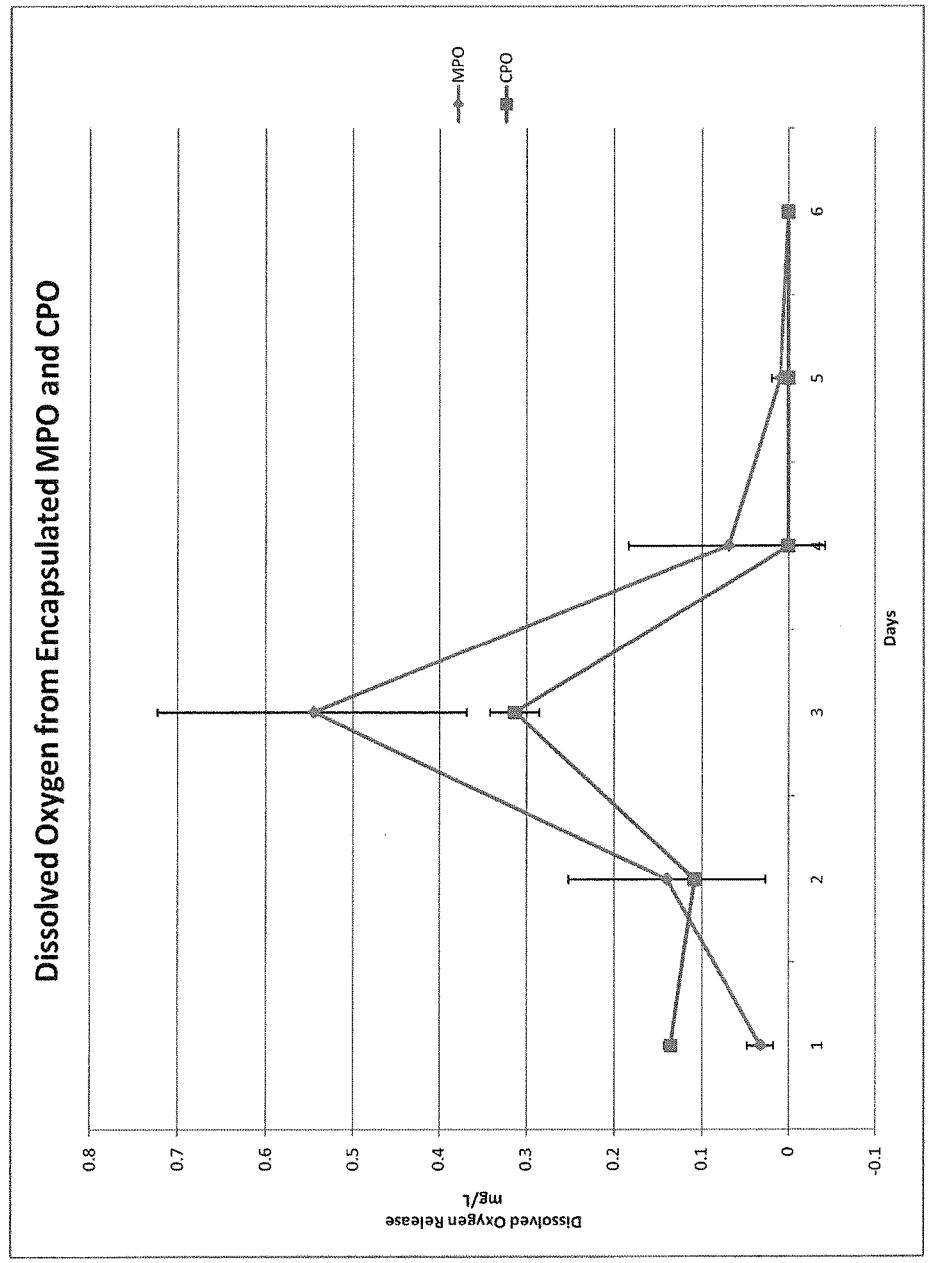
Figure 1: Comparison of $CaO_2$ and $MgO_2$ release over six days, dissolved oxygen readings are an average of 5 sample groups with 1500 microcapsules each.

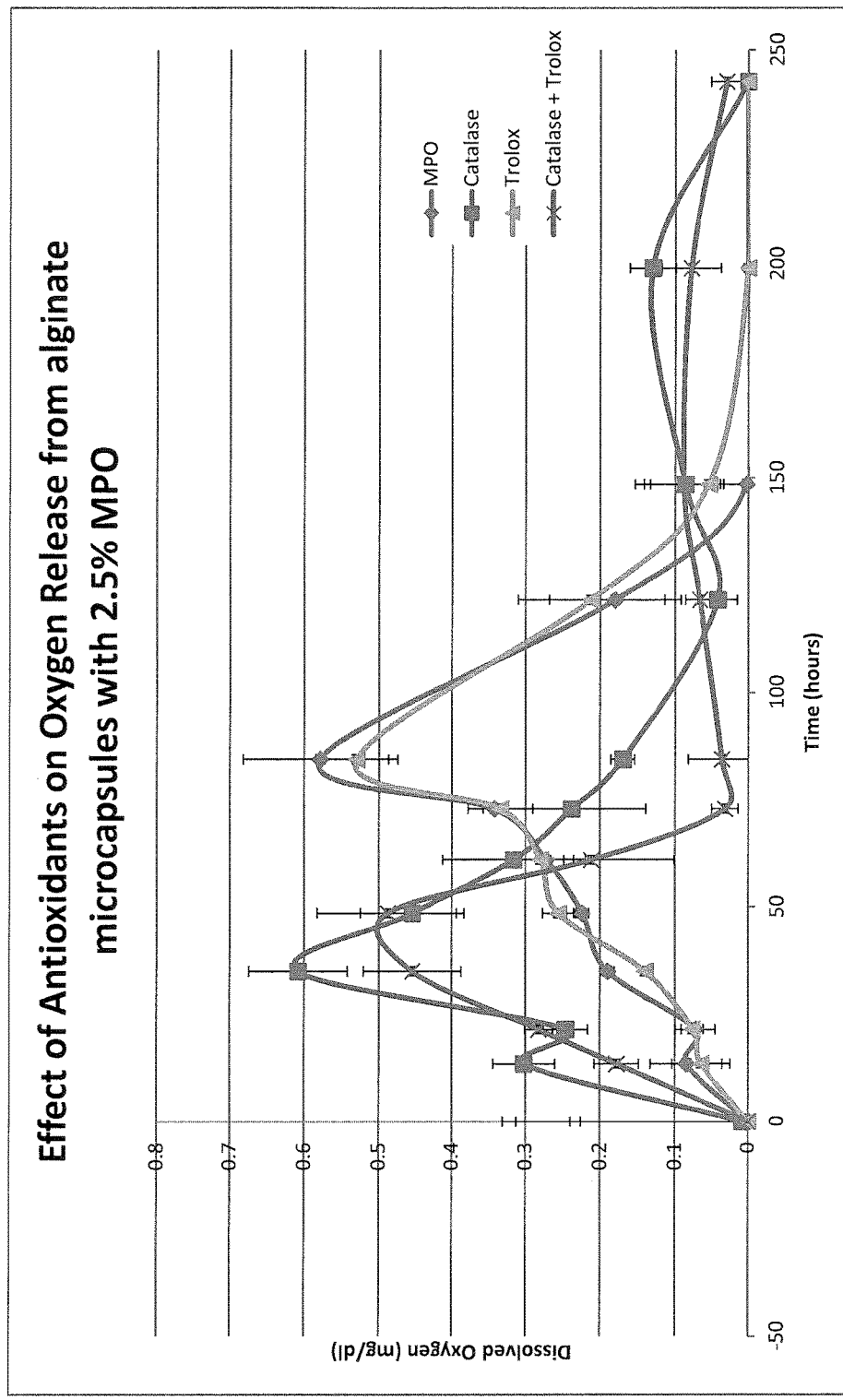
Figure 2: Effect of antioxidants of Oxygen release from alginate microcapsules with 2.5 % MPO.

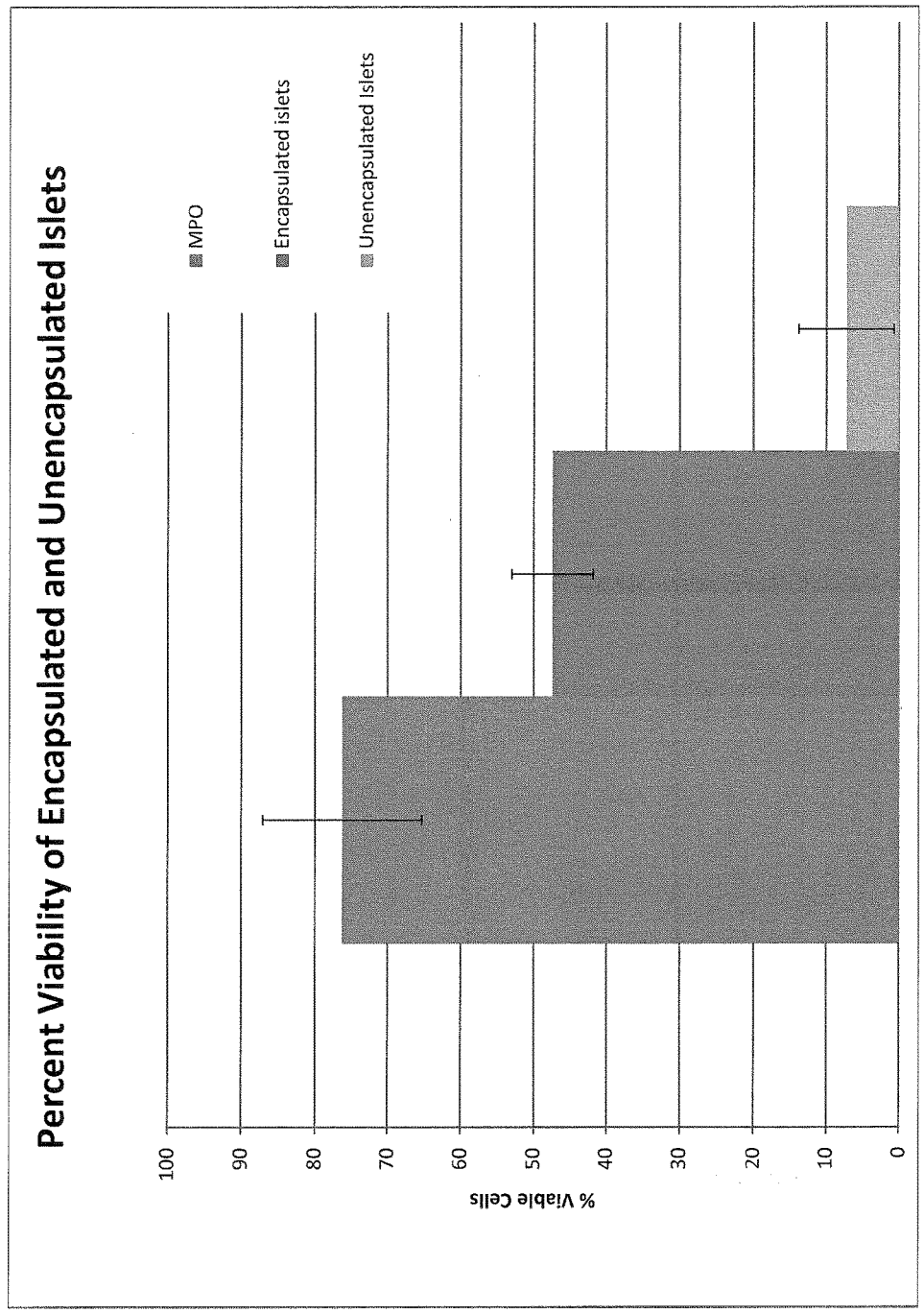
Figure 3: Quantative analysis of confocal images.

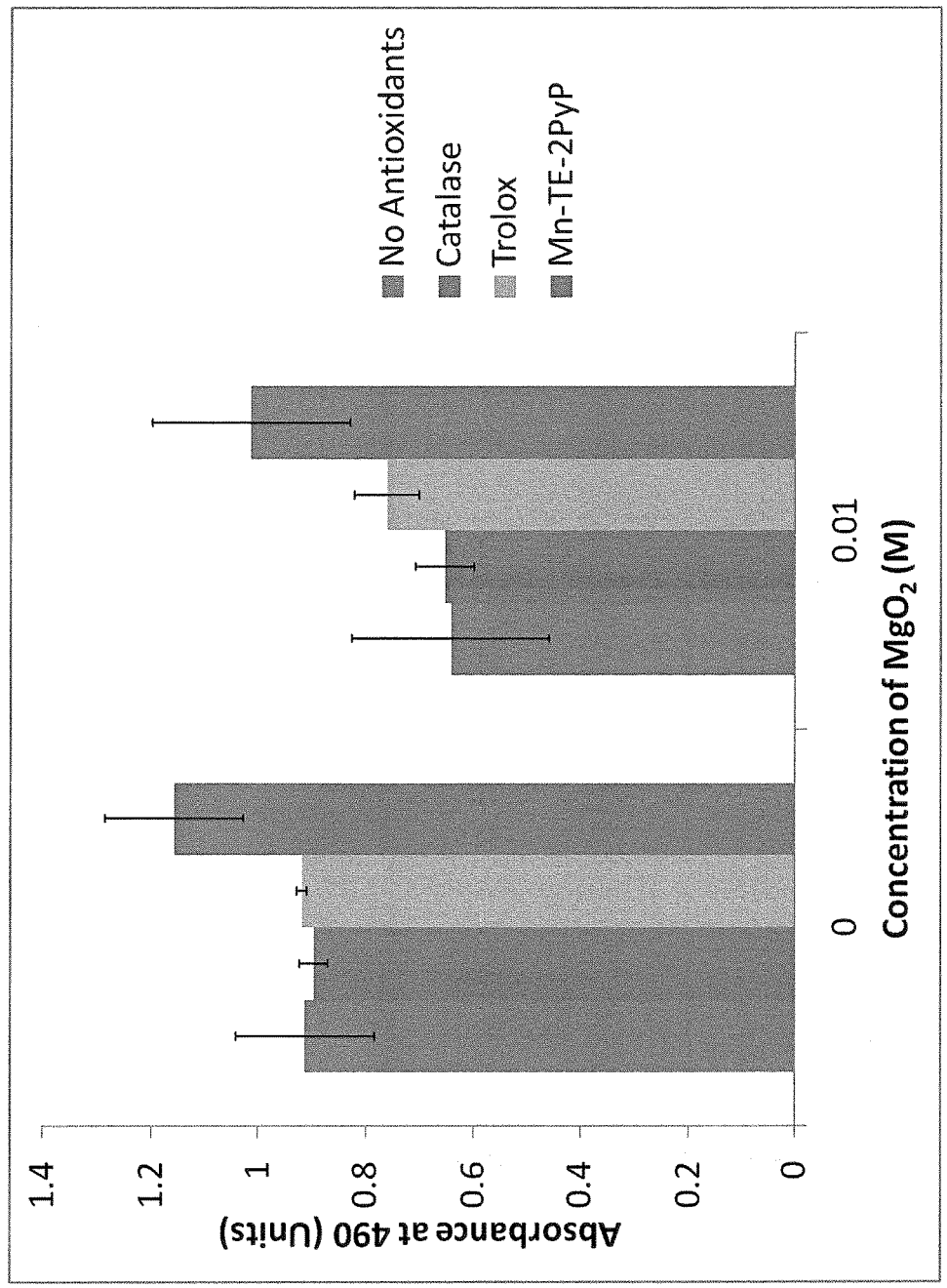
Figure 4: Viability of islets co-cultured with MPO and antioxidants.

CO-ENCAPSULATION OF LIVE CELLS WITH OXYGEN-GENERATING PARTICLES

RELATED APPLICATIONS

This application is a continuation of U.S. patent application Ser. No. 15/411,351, filed Jan. 20, 2017, now allowed, which is a continuation of U.S. patent application Ser. No. 15/183,037, filed Jun. 15, 2016, now U.S. Pat. No. 9,561,254, which is a continuation of U.S. patent application Ser. No. 14/237,214, filed May 13, 2014, now U.S. Pat. No. 9,393,272, which is a 35 U.S.C. § 371 national phase entry of PCT Application PCT/US2012/050060, filed Aug. 9, 2012, and published in English on Feb. 14, 2013, as International Publication No. WO 2013/023013, and which claims the benefit of United States Provisional Patent Application No. 61/601,780, filed Feb. 22, 2012, and United States Provisional Patent Application Ser. No. 61/521,420, filed Aug. 9, 2011, the disclosure of each of which is incorporated herein by reference in its entirety.

BACKGROUND OF THE INVENTION

Glycemic control in diabetes has been shown to delay the onset of, and slow the progression of, associated pathological complications. However, achieving adequate glycemic control using insulin therapy can be difficult. One alternative to insulin therapy is the transplantation of functioning pancreatic islet cells to diabetic subjects, to provide biological insulin replacement. However, transplanted or grafted islet cells encounter immunological rejection, which can limit the clinical usefulness of his method. Microencapsulation of islet cells has been proposed to reduce or avoid immunological rejection of transplanted islet cells. See, e.g., U.S. Pat. No. 6,783,964 to Opara. There remains a need, however, for new ways to facilitate the effective implantation of live encapsulated pancreatic islet cells for the treatment of diabetes.

SUMMARY OF THE INVENTION

A first aspect of the present invention is a microcapsule comprising: (a) a liquid aqueous or hydrogel core; (b) a semipermeable membrane surrounding that core; (c) live animal cells in the core; and (d) oxygen-generating particles in said core, the oxygen-generating particles included in said microcapsules in an amount sufficient to lengthen the duration of viability (e.g., lengthen the life-span) of the animal cells in the microcapsules.

In some embodiments, the oxygen-generating particles comprise a biodegradable polymer (e.g., from 0.1 to 15 or 30 percent by weight) in combination with an inorganic peroxide (e.g., from 40 to 99 percent by weight).

In some embodiments, the inorganic peroxide is selected from the group consisting of calcium peroxide, magnesium peroxide, sodium peroxide, sodium percarbonate, benzylperoxide, and combinations thereof.

In some embodiments, the oxygen-generating particles and/or the microcapsules further comprise an antioxidant, a radical trap, and/or a peroxide decomposition catalyst (e.g., (2, 2,6,6-tetramethylpiperidin-1-yl)oxidanyl, catalase, ascorbic acid) (e.g., from zero to 30 percent by weight).

In some embodiments, the microcapsules further comprising an auxiliary layer surrounding the semipermeable layer.

In some embodiments, the auxiliary layer comprises a biodegradable polymer, said biodegradable polymer optionally containing an active compound (e.g. angiogenic proteins, antibodies, hormones, polypeptides, amino acids, neurotransmitters, neurotoxins, viruses, cytokines, and nucleic acids).

In some embodiments, the said auxiliary layer contains a pro-angiogenic agent in an amount effective to enhance the growth of blood vessels adjacent said microcapsule (e.g., after in vivo implantation thereof in a mammalian subject, such as for carrying out a method as described herein).

In some embodiments, the animal cells are mammalian cells.

In some embodiments, the mammalian cells are pancreatic islet cells, ovarian cells (e.g., granulosa and/or theca cells) hepatocytes, myocytes, alveoli, neuronal cells, and/or adrenal cells.

A further aspect of the invention is a composition comprising or consisting essentially of microcapsules as described herein in a pharmaceutically acceptable carrier.

A further aspect of the invention is a method of treating diabetes in a subject in need thereof, comprising implanting microcapsules as described herein in said subject in a treatment-effective amount.

A further aspect of the invention is microcapsules as described herein for use in treating diabetes in a subject in need thereof.

Implantation of oxygen-generating particles is described, for example, in US Patent Application No. US 2010/0112087 to Harrison et al. (May 6, 2010), for the purpose of treating hypoxic tissue. However, the co-encapsulation of oxygen generating particles with live cells is neither suggested nor described.

The present invention is explained in greater detail in the drawings herein and the specification set forth below. The disclosures of all United States patent references cited herein are to be incorporated by reference herein in their entirety.

BRIEF DESCRIPTION OF THE DRAWINGS

FIG. 1: Comparison of $CaO_2$ and $MgO_2$ release over six days, dissolved oxygen readings are an average of 5 sample groups with 1500 microcapsules each; measurements were taken in a hypoxic chamber.

FIG. 2: Effect of antioxidants on oxygen release from alginate microcapsules with 2.5% MPO. In the presence of 100 U/ml catalase and 100 U/ml Catalase+1.5 mM Trolox the oxygen release is significantly shortened compared to the release of MPO alone. However this effect is not observed with 1.5 mM Trolox alone.

FIG. 3: Quantative analysis of confocal images. Each group is the average of 3 cells selected at random, error bars represent standard deviation.

FIG. 4: Viability of islets co-cultured with MPO and antioxidants. Isolated human islets were co-cultured with 10 mM MPO for 2 days in normal culture conditions with the following antioxidants: 100 Units/mL Catalase, 1.5 mM Trolox and 30 µM MnTE-2-Pyp. After the two day culture period islet viabilty was determined with an MTS assay. Error bars represent standard deviation, n=5.

DETAILED DESCRIPTION OF THE PREFERRED EMBODIMENTS

"Subjects" as used herein are, in general, mammalian subjects. While human subjects are preferred, the subjects may in some embodiments be other animals, such as dogs and cats for veterinary purposes. Subjects are generally female. While the subjects may be of any suitable age, the subjects are typically adults and in some embodiments are menopausal female subjects.

"Treat" as used herein refers to any type of treatment that imparts a benefit to a subject, including but not limited to delaying the onset or reducing the severity of at least one symptom in the subject "Pharmaceutically acceptable" as used herein means that the compound or composition is suitable for administration to a subject to achieve the treatments described herein, without unduly deleterious side effects in light of the severity of the disease and necessity of the treatment.

"Biologically active compound" as used herein may be any suitable compound, including but not limited to TGF-beta, basic fibroblast growth factor (FGF2), epithelial growth factor (EGF), insulin-like growth factor-1 (IGF-1), transforming growth factors alpha and beta (TGF-1 alpha and beta), nerve growth factor (NGF), platelet-derived growth factor (PDGF), vascular endothelial growth factor/ vascular permeability factor (VEGF/VPF), anti-virals, anti-bacterials, anti-inflammatory, immuno-suppressants, analgesics, vascularizing agents or pro-angiogenic agents, and cell adhesion molecules, and combinations thereof See, e.g., US Patent Application No. 20110052715 (Mar. 3, 2011).

1. Cells.

Cells used to carry out the present invention are, in general, live mammalian cells collected from a suitable donor. Donors are, in general, mammalian (e.g., human, dog, cat, rabbit, rat, mouse, monkey, chimpanzee, horse, pig, goat, sheep). The donor may be of the same species as the subject being treated, or of a different species. In some embodiments the donor may be the same subject undergoing treatment, where suitable cells were harvested from the subject and stored for subsequent use.

Cells are isolated from donors and cultured for microcapsule production as desired in accordance with techniques known in the art. See, e.g., Sanjay K. Agarwal et al., *Leptin Antagonizes the Insulin-Like Growth Factor-I Augmentation of Steroidogenesis in Granulosa and Theca Cells of the Human Ovary*, J. Clin Endocrinol Metab 84: 1072-1076 (1999); Jon C. Havelock et al., Ovarian granulosa cell lines, Molecular and Cellular Endocrinology 228, 67-78 (2004); Jessica K. Wickenheisser et al., *Human ovarian theca cells in culture*, Trends in Endocrinology & Metabolism 17, 65-71 (2006). In general, fresh tissue is divided by mincing, teasing, comminution and/or collagenase digestion. The desired cells are then isolated from contaminating cells and materials by washing, filtering, centrifuging or picking procedures, and optionally cultured and/or cryopreserved as desired prior to encapsulation.

2. Oxygen-generating Particles.

Any suitable oxygen-generating particle can be used to carry out the present invention, including but not limited to encapsulated hydrogen peroxide, inorganic peroxides, or peroxide adducts such as described in US Patent Application Publication Nos. 2009/0169630 to Ward et al. and 2010/0112087 to Harrison et al. (the disclosures of which are incorporated by reference herein in their entirety). The oxygen-generating particles preferably comprise an organic or inorganic peroxide such as urea peroxide, calcium peroxide, magnesium peroxide, and/or sodium percarbonate. The oxygen-generating active agent is included in the composition in any suitable amount (e.g., from 0.1 or 1 to 10, 20, or 30 percent by weight, or more). In some embodiments calcium peroxide is preferred as it releases oxygen at a desireable rate in situ. The oxygen-generating active agent can be included in the polymer in solid form, such as in the form of a plurality of solid particles thereof.

In some embodiments a radical trap or peroxide or radical decomposition catalyst is also included in the oxygen-generating particle and/or the microcapsule composition (e.g., in an amount of from 0.1 or 1 to 10, 20 or 30 percent by weight, or more). Suitable examples of radical traps or decomposition catalysts include, but are not limited to, iron (including, but not limited to, iron particles or nanoparticles, enzymes such as catalase, peroxidase, or dehydrogenase (see, e.g., U.S. Pat. No. 7,189,329), compounds such as cyclic salen-metal compounds that have superoxide and/or catalase and/or peroxidase activity (see, e.g., U.S. Pat. No. 7,122,537), etc.). The radical trap or decomposing catalyst may be included in solid form (e.g., solid particulate form) and can be coated on or incorporated in the polymer, or both coated on and incorporated in the polymer).

3. Microcapsule Production.

Encapsulation of live cells in combination with oxygen-generating particles can be carried out in accordance with known techniques or variations thereof that will be apparent to those skilled in the art. See, e.g., US Pat. Nos. 6,783,964 and 6,365,385 to Opara, the disclosures of which are incorporated by reference herein in their entirety.

Microcapsules useful in the present invention optionally, but in some embodiments preferably, have at least one semipermeable membrane surrounding a cell-containing interior (preferably a hydrogel interior). The semipermeable membrane permits the diffusion of nutrients, biologically active molecules and other selected products through the surface membrane and into the microcapsule core. The surface membrane contains pores of a size that determines the molecular weight cut-off of the membrane. The membrane pore size is chosen to allow the passage of active agents secreted by the cells (e.g., insulin from pancreatic cells; estrogen, and in some embodiments progesterone, from ovarian cells; etc.) from the within the capsule to the external environment, but to exclude the entry of host immune response factors (where the encapsulated cells are not autologous). Such a semipermeable membrane is typically formed from a polycation such as a polyamine (e.g., polylysine and/or polyornithine), as discussed further below.

In one non-limiting example embodiment of an encapsulation technique, U.S. Pat. No. 4,391,909 to Lim et al describes a method in which cells are suspended in sodium alginate in saline, and droplets containing cells are produced. Droplets of cell-containing alginate flow into calcium chloride in saline. The negatively charged alginate droplets bind calcium and form a calcium alginate gel. The microcapsules are washed in saline and incubated with poly-L-lysine or poly-L-ornithine (or combinations thereof); the positively charged poly-l-lysine and/or poly-L-ornithine displaces calcium ions and binds (ionic) negatively charged alginate, producing an outer poly-electrolyte semipermeable membrane. An exterior coating of sodium alginate may be added by washing the microcapsules with a solution of sodium alginate, which ionically bonds to the poly-L-lysine and/or poly-L-ornithine layer (this serves to reduce any inflammatory response that may be provoked in the subject by contact of the polycationic membrane to tissue). This technique produces what has been termed a "single-wall" microcapsule. A "double-wall" microcapsule can be produced by following the same procedure as for single-wall microcapsules, but prior to any incubation with sodium citrate, the microcapsules are again incubated with poly-l-lysine and sodium alginate.

In additional non-limiting examples of encapsulation methods, Chang et al., U.S. Pat. No. 5,084,350 discloses microcapsules enclosed in a larger matrix, where the microcapsules are liquefied once the microcapsules are within the larger matrix. Tsang et al., U.S. Pat. No. 4,663,286 discloses encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core. U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginate/polylysine microcapsules incorporating a graft copolymer of poly-l-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate. U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine. U.S. Pat. No. 5,846,530 to Soon-Shiong describes microcapsules containing cells that have been individually coated with polymerizable alginate, or polymerizable polycations such as polylysine, prior to encapsulation.

When desired, the alginate-polylysine microcapsules can be incubated in sodium citrate to solubilize any calcium alginate that has not reacted with poly-l-lysine, i.e., to solubilize the internal core of sodium alginate containing the cells, thus producing a microcapsule with a liquefied cell-containing core portion. See Lim and Sun, *Science* 210:908 (1980). Such microcapsules are referred to herein as having "chelated", "hollow" or "liquid" cores.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. See, e.g., U.S. Pat. No. 6,783,964 to Opara.

One currently preferred method for the production of microcapsules is described in O. Khanna et al., *Synthesis of multilayered alginate microcapsules for the sustained release of fibroblast growth factor-1* J. Biomed. Mater. Res. Part A: 95A: 632-640 (2010).

Microcapsules may be of any suitable size, such as from 10, 20 or 30 microns in diameter, up to 1000, 2000, or 5000 microns in diameter. Microcapsules may contain any suitable amount of cell. For example, in some embodiments, the cells are included in the microcapsules in an amount of from 1,000 or 2,000 cells per microcapsule up to $1\times10^6$, $1\times10^8$, or $1\times10^9$ cells per microcapsule; and the theca cells are included in the microcapsules an amount of from 1,000 or 2,000 cells per microcapsule up to $1\times10^6$, $1\times10^8$, or $1\times10^9$ cells per microcapsule.

In some embodiments an antioxidant is also included in the microcapsule and/or the oxygen-generating particle composition (e.g., in an amount of from 0.1 or 1 to 10, 20 or 30 percent by weight, or more). Suitable examples of antioxidants include, but are not limited to, ascorbic acid or vitamin C, tocopherols and tocotrienols such as vitamin E and analogs thereof such as 6-hydroxy-2,5,7,8-tetramethyl-chroman-2-carboxylic acid (also known as "TROLOX"), porphyrin or metalloporphyrin antioxidants, particularly manganese porphyrin superoxide dismutase/catalase mimetics such as Mn (III) tetrakis (N-ethylpyridinium-2-yl) porphyrin (MnTE-2-PyP) (see, e.g., R. Rosenthal et al., *J. Biol. Inorg. Chem.* 14: 979-991 (2009); see also U.S. Pat. No. 5,994,339 to Crapo et al.; U.S. Pat. No.6,127,356 to Crapo et al.; and U.S. Pat. No. 8,067,405 to Klimko et al.), phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen, etc., including combinations thereof, See, e.g., U.S. Pat. Nos. 7,999,003 and 5,928,654.

Microcapsules of the present invention may be administered after production, refrigerated and/or cryopreserved for subsequent use, and/or cultured for subsequent use, as desired. Microcapsules of the invention may be washed (e.g., in sterile physiological saline solution) prior to formulation and/or administration, as needed depending upon their manner of production.

4. Formulation, Administration and Uses.

Microcapsules of the present invention may be administered per se or formulated for administration by any suitable technique, such as by mixing with sterile physiological saline solution. The microcapsules may be administered by any suitable technique, including but not limited to surgical implantation or injection (either of which may be carried out subcutaneously, intraperitoneally, intramuscularly, or into any other suitable compartment. Dosage of cells administered can be determined in accordance with known techniques or variations thereof that will be apparent to those skilled in the art. For comparison, in the treatment of diabetes, the International Islet Transplant Registry has recommended transplants of at least 6,000 cells per kilogram of recipient body weight, to achieve euglycemia. In the present invention, the number of cells implanted will depend upon the age and condition of the subject, the particular disorder being treated, etc. In some embodiments of the present invention, from 1,000, 2,000, 3,000, or 6,000 cells per kilogram of recipient body weight, up to 20,000, 40,000 or 60,000 cells per kilogram recipient body weight, are administered.

While the present invention is described primarily with reference to the encapsulation of pancreatic islet cells for the treatment of diabetes (including type I and type II diabetes), it will be appreciated that a variety of different cell types can advantageously be co-encapsulated with oxygen-generating particles in the manner described herein. For example, any of a variety cells types, particularly stem cells (e.g., mesenchymal stem cells isolated from bone marrow, muscle tissues, dermis, or combinations thereof) for encapsulation in injectable particles for tissue construction, reconstruction or repair, as described in U.S. Pat. No. 7,338,657 to Vogel.

Microcapsules of the present invention that contain ovarian granulosa and theca cells may be administered to subjects as a treatment for any condition in which estrogen replacement therapy is used. Subjects or patients to be treated by such methods include subjects afflicted with, or at increased risk of, one or more of osteoporosis, hot flashes, irregular period, vaginal atrophy, vaginal and/or bladder infection, incontinence (e.g., urge incontinence, stress incontinence), fatigue, sleep disturbances, irritability, mood swings, depression, loss of muscle mass, increased fat tissue, thinning and loss of skin elasticity, loss of bone tissue, impaired cognition etc., which may be associated with menopause, hysterectomy, ovarectomy, or other condition for which estrogen or hormone replacement therapy is employed, The present invention is explained in greater detail in the following non-limiting Examples.

EXAMPLE 1

Co-Encapsulation of Islet Cells with Particulate Oxygen Generating Substances (POGS)

Transplanted islets are subjected to extended periods of hypoxia following the process of isolation, purification, and transplantation, which affects their survival rates. The goal of the present study was to explore the potential use of particulate oxygen generating substances (POGS) to enhance the viability of encapsulated islets for transplantation.

Materials: Calcium Peroxide,$CaO_2$ (CPO), Magnesium Peroxide,$MgO_2$, (MPO), Catalase (from bovine liver), Trolox (Sigma-Aldrich, USA), Calcium chloride, HEPES, Zinc Sulfate, Histopaque-1083, and HBSS were purchased from Sigma-Aldrich (USA). CMRL-1066, and all reagents for the human isolation unless otherwise noted were purchased from Cellgro (Manassas, Va.). ITS plus medium was purchased from BD (Franklin Lakes, N.J.). L-glutamate and penicillin/streptomycin were purchased from Gibco (USA). Clzyme Collagenase was purchased from VitaCyte (Indianapolis, Ind.). Low viscosity (20-200 mPa s) ultra-pure sodium alginate with high mannuronic acid content (LVM) were purchased from Nova-Matrix (Oslo, Norway) which was reported by the manufacturer to have molecular weights 75-200 kDa and a G/M ratio of ≤1.

Human Islet Isolation, Purification and Culture: Human islets were isolated from cadaveric human pancreases using the Ricordi technique (J. Lakey et al., *Current Human Islet Isolation Protocol.* 1 edn, (Medical Review Co. 2004)) with collagenase digestion of tissue, and following purification using a COBE 2991 and a histopaque gradient, were maintained for 24 hours under standard cell culture conditions in Memphis Serum Free Media (MSFM)(A. Gaber and D. Fraga, Advances in long-term islet culture-The Memphis experience. *Cell Biochem. Biophys.*, 49-54 (2004)) prior to encapsulation.

Comparison of CPO and MPO: We first examined the oxygen release profiles of two POGS, CPO and MPO encapsulated in alginate microbeads in the absence or presence of catalase (100 U/ml), and the antioxidant, Trolox (1.5 mM). Sieves were used to select both MPO and CPO particles equal to and less than 25 μm in diameter. Then 0.5% by weight solution of 1.5% LVM and either CPO or MPO were prepared respectively. These solutions were then extruded through an encapsulating device forming microspheres measuring 300 to 400 μM in diameter, which were allowed to crosslink for 15 minutes in 1.1% $CaCl_2$ solution. After cross-linking, the microbeads were rinsed with HBSS and placed into 50 ml conical tubes (BD, USA) containing 20 mL ultra pure water with 10 mM HEPES (pH=7.4). Tubes were placed in a 1% oxygen environment in a hypoxic glovebox system (Biospherix, USA) with the caps of the tubes removed allowing for gas exchange. Dissolved oxygen readings were taken every 24 hours for 6 days using an Orion 4-star DO Probe (Thermo Science).

Oxygen release from MPO Alginate Capsules: On the basis of a better release profile, we then selected $MgO_2$ for further studies. First the release profiles of various concentrations of MPO were measured. Using the same technique as described above 0%, 0.25%, 0.5%, 1%, 1.5%, 2.0%, 2.5%, 5%, 10%, 20%, 30%, and 40% (by weight) solutions of MPO in 1.5% UP LVM were prepared, with particles larger than 25 μM sieved out of the solution prior to encapsulation. The MPO particles in the solutions were then encapsulated and placed into the hypoxic chamber in 50 ml conical tubes. Dissolved oxygen levels were measured for up to 250 hours. Using the same methodology we then assessed the effect of the antioxidants, Catalase and Trolox, on oxygen release. A 2.5% solution of MPO and 1.5% LVM was prepared, and was mixed with 50, 100, and 200 U/ml of catalase, 0.5, 1.0, and 1.5 mM Trolox respectively. Capsules were prepared and dissolved oxygen levels were measured as described earlier. Lastly the combined effects of Trolox and Catalase were investigated; capsules were prepared with 2.5% MPO, and 1.5% LVM and 0.5 mM+50 U/ml, 1.5 mM+100 U/ml, and 3.0 mM+200 U/ml Trolox and Catalase respectively. Dissolved oxygen levels were measured for up to 250 hours.

Islet Encapsulation: After 24 hours of culture, islets were mixed at a concentration of 1000 islets/ml with 1.5% ultra pure low-viscosity high mannuronic acid (LVM) alginate (with or without 2.5% $MgO_2$, 100 U/ml catalase and 1.5 mM Trolox). Each islet suspension was then separately extruded through a microfluidic device at a flow rate of 1.4 ml/min and an air pressure of 15 psi to generate microbeads with a mean+SD diameter of 400±100 um. The microbeads were allowed to crosslink for 15 minutes in a solution of 1.1% $CaCl_2$ and 10 mM HEPES and were then rinsed with HBSS and cultured in MSFM for 24 hours under standard culture conditions. Naked islets (control) and encapsulated islets were stained for Live/Dead viability assay with carboxyfluorescein diacetate (CFDA) and propidium iodide (PI) after an additional 24 hours culture. Confocal microscopy was used to image the stained islets and viability was quantified by counting the percentage of live cells over the total number of cells with Image J. Results were statistically analyzed using a one-way ANOVA with Tukey post test.

Results and Discussion: We found that MPO provided a higher release of oxygen for up to five days compared to CPO, FIG. 1. We found that the duration of oxygen release from alginate microbeads containing $MgO_2$ was significantly shortened by the presence of catalase alone or in combination with Trolox; however there was no significant change in oxygen release by MPO in the presence of Trolox alone (FIG. 2). The % mean±SD viability of naked unencapsulated islets was significantly lower (7.1±6) than encapsulated islets alone (47.4±5.6) ($p<0.01$, n=3). The viability of encapsulated islets with $MgO_2$, Catalase, and Trolox was significantly higher (76.2±10.9) than that measured in encapsulated islets without $MgO_2$ ($p<0.05$) (FIG. 3).

Conclusion: In summary, we found that the 3D environment of microbeads enhanced the viability of islets in culture and that $MgO_2$ enhanced encapsulated islet cell viability further in the presence of antioxidants, as oxygen released from POGS was readily available to the islets.

EXAMPLE 2

Inclusion of a SOD-mimicking Catalytic Antioxidant with Co-Encapsulated Islet Cells and POGS Previous studies have shown that the isolation process predisposes islets to subsequent damage and functional impairment and that an SOD mimicking catalytic antioxidant, MnTE-2-PyP (also called AEOL10113), developed by Drs. Piganelli and Crapo, can be beneficial in preserving islet cell functional mass when used in the isolation or culture medium (R. Bottino et al., *Preservation of human islet cell functional mass by antioxidative action of a novel SOD mimic compound*. Diabetes 51: 2561 (2002); R. Bottino et al., Diabetes 53: 2559 (2004)). We have found that MnTE-2-PyP significantly ($p<0.05$) enhances the viability of isolated human islets when added to islets in normal culture (FIG. 4). In FIG. 4, we still further show that MnTE-2-PyP counteracts the diminishing effect of MPO on islet viability.

The foregoing is illustrative of the present invention, and is not to be construed as limiting thereof The invention is defined by the following claims, with equivalents of the claims to be included therein.

That which is claimed is:

1. A microcapsule comprising:
   (a) a liquid aqueous or hydrogel core;
   (b) a semipermeable membrane surrounding said core;
   (c) live animal cells in said core, wherein said live animal cells are mammalian cells selected from the group consisting of ovarian cells, hepatocytes, alveoli, neuronal cells and adrenal cells; and
   (d) oxygen-generating particles in said core, said oxygen-generating particles included in said microcapsules in an amount sufficient to lengthen the duration of viability of said animal cells in said microcapsules, wherein the oxygen-generating particles comprise an inorganic peroxide, said inorganic peroxide is selected from the group consisting of calcium peroxide, magnesium peroxide, sodium peroxide, sodium percarbonate, benzylperoxide, and combinations thereof, and wherein the microcapsule further comprises an antioxidant, and the antioxidant is selected from the group consisting of a metalloporphyrin antioxidant, 6-hydroxy-2,5,7,8-tetramethylchroman-2-carboxylic acid, ascorbic acid, and flavonoids.

2. The microcapsule of claim 1, wherein said oxygen-generating particles further comprise a radical trap or peroxide decomposition catalyst.

3. The microcapsule of claim 1, said microcapsule further comprising an auxiliary layer surrounding said semipermeable layer.

4. The microcapsule of claim 3, wherein said auxiliary layer comprises a biodegradable polymer, said biodegradable polymer optionally containing an active compound.

5. The microcapsule of claim 4, wherein said auxiliary layer contains a pro-angiogenic agent in an amount effective to enhance the growth of blood vessels adjacent said microcapsule.

6. The microcapsule of claim 1, wherein said mammalian cells are ovarian cells.

7. The microcapsule of claim 1, wherein said mammalian cells are hepatocytes.

8. The microcapsule of claim 1, wherein said mammalian cells are alveoli.

9. A composition comprising a plurality of microcapsules of claim 1.

10. The composition of claim 9, further comprising a pharmaceutically acceptable carrier.

11. The microcapsule of claim 1, wherein said mammalian cells are neuronal cells.

12. The microcapsule of claim 1, wherein said mammalian cells are adrenal cells.

* * * * *